US012024617B2

United States Patent
Chen et al.

(10) Patent No.: US 12,024,617 B2
(45) Date of Patent: Jul. 2, 2024

(54) CELLULOSE COMPOSITION

(71) Applicant: EVOPHANCIE BIOTECH LTD, New Taipei (TW)

(72) Inventors: Chao-Cheng Chen, New Taipei (TW); Chi-Hsiang Lu, New Taipei (TW); Jun-Wei Hong, New Taipei (TW); Shang-Ru Lin, New Taipei (TW)

(73) Assignee: EVOPHANCIE BIOTECH LTD, New Taipei (TW)

( * ) Notice: Subject to any disclaimer, the term of this patent is extended or adjusted under 35 U.S.C. 154(b) by 165 days.

(21) Appl. No.: 16/777,949

(22) Filed: Jan. 31, 2020

(65) Prior Publication Data

US 2020/0247978 A1     Aug. 6, 2020

(30) Foreign Application Priority Data

Feb. 1, 2019   (TW) ................................ 108104284

(51) Int. Cl.
| | | |
|---|---|---|
| *C08L 1/02* | (2006.01) | |
| *A61K 8/02* | (2006.01) | |
| *A61K 8/60* | (2006.01) | |
| *A61K 8/73* | (2006.01) | |
| *A61K 9/00* | (2006.01) | |
| *A61K 47/38* | (2006.01) | |
| *A61Q 19/00* | (2006.01) | |
| *A61Q 19/02* | (2006.01) | |
| *A61Q 19/08* | (2006.01) | |
| *C05F 11/00* | (2006.01) | |
| *C08L 1/04* | (2006.01) | |
| *C12P 19/04* | (2006.01) | |

(52) U.S. Cl.
CPC ................. *C08L 1/02* (2013.01); *A61K 8/02* (2013.01); *A61K 8/0216* (2013.01); *A61K 8/602* (2013.01); *A61K 8/731* (2013.01); *A61K 9/0087* (2013.01); *A61K 47/38* (2013.01); *A61Q 19/00* (2013.01); *A61Q 19/007* (2013.01); *A61Q 19/02* (2013.01); *A61Q 19/08* (2013.01); *C05F 11/00* (2013.01); *C08L 1/04* (2013.01); *C12P 19/04* (2013.01); *C08L 2201/06* (2013.01); *C08L 2203/02* (2013.01); *C08L 2205/025* (2013.01)

(58) Field of Classification Search
None
See application file for complete search history.

(56) References Cited

U.S. PATENT DOCUMENTS

| | | | |
|---|---|---|---|
| 2015/0216784 A1 | 8/2015 | Lin et al. | |
| 2015/0297469 A1 | 10/2015 | Hayashi et al. | |
| 2017/0368225 A1* | 12/2017 | Gatenholm | ......... A61L 27/3882 |

FOREIGN PATENT DOCUMENTS

| | | | | |
|---|---|---|---|---|
| CN | 104825343 | | 8/2015 | |
| CN | 110128803 A | * | 8/2019 | .............. C08L 67/04 |
| JP | 2014-209878 | | 11/2014 | |
| JP | 2016-146778 | | 8/2016 | |
| JP | 2016-147825 | | 8/2016 | |
| WO | 2004/088034 | | 10/2004 | |

OTHER PUBLICATIONS

Ougiya et al.("Relationship between Suspension Properties and Fibril Structure of Disintegrated Bacterial Cellulose", Bioscience, Biotenology, and Biochemistry, vol. 62(9) (1998), p. 1714-1719). (Year: 1998).*
"High Quality Gold Nanoparticles for Better Results" (an internet article by Nano Hybrids obtained from the website https://nanohybrids.net/pages/differences-between-optical-density-absorbance-and-extinction-of-gold-nanoparticles.*
Li et al ("Solute Concentration-Dependent Contact Angle Hysteresis and Evaporation Stains", Langmuir, vol. 30 (26) (2014), p. 7716-7723) (Year: 2014).*
English translation for CN 110128803A (Year: 2019).*
Costa et al.("Production of Bacterial Cellulose by Gluconacetobacter hansenii Using Corn Steep Liquor As Nutrient Sources", Frontiers in Microbiology, vol. 8 (Oct. 17, 2017), p. 1-12). (Year: 2017).*
Taiwanese Office Action for Taiwanese Patent Application No. 108104284 dated Apr. 10, 2020.
Abdelhaby, et al., Bacterial Cellulose Production as Affected by Bacterial Strains and Some Fermentation Conditions, Nature and Science 2015; 13(3).
Japanese Office Action for Japanese Patent Application No. 2020-016086 dated Dec. 22, 2020.

* cited by examiner

Primary Examiner — Sin J Lee
(74) Attorney, Agent, or Firm — Amin, Turocy & Watson, LLP

(57) ABSTRACT

Provided is a cellulose composition, including a plurality of biocelluloses, wherein a diameter of the biocelluloses ranges from 20 to 30 nanometer, and a length of the biocelluloses ranges from 2000 to 3000 nanometer. The biocelluloses have good biocompatibility and can effectively enhance the efficiency of absorption and transmission of substances.

7 Claims, No Drawings

CELLULOSE COMPOSITION

BACKGROUND

1. Technical Field

The present disclosure relates to cellulose compositions, and more particularly, to a cellulose composition for improving the absorption and transport efficiency of a substance.

2. Description of the Related Art

Biocellulose refers to a fiber which is excreted by extracellular secretion after the microorganism utilizes a carbon source in a culture solution to form a β-1,4-glucan chain in a cell. Due to the properties of good hydrophilicity, high mechanical strength and high biocompatibility, the biocellulose can be applied in the medical field of wound dressings and cosmetics field, in favor of permeation of moisture and gas on skin surface and absorption of secretions.

The production of biocellulose is mainly carried out by cultures in a manner of stirring fermentation and static fermentation, and the layered or block-shaped biocelluloses are further purified, sterilized and added with active ingredients to form a layered material for further application of backend product.

Recently, in order to break through the limitations of the product application, a mechanical treatment has been developed to break the layered or massive biocellulose material to form a continuous medium and increase the contact area of the biocellulose, so that the efficiency of absorption and transmission of the biocellulose is multiplied. The related technology is disclosed in the Taiwanese patent No. 1586373. However, in the breakage and disintegration process, the specific surface area of the biocellulose is increased, and the viscosity of the treatment is also increased, which increases the treatment difficulty, limiting the biocellulose breakage and disintegration to a certain degree only. Although the process of Taiwanese patent No. 1586373 teaches the breakage and disintegration process for the biocellulose material in a homogeneous manner, it actually causes easily a blocking problem by the material in practical application. Even if the diluted concentration of the homogenizing solution alleviates the problem, the degree of shear fracture of the biocellulose cannot be further increased, limiting the effect of transdermal absorption and transport of substances, resulted from the increased specific surface area.

Therefore, there exists a need for a cellulose composition which can effectively improve the absorption and transport efficiency of a substance and a method for stably producing the cellulose composition, so as to solve the problems existing in the current techniques.

SUMMARY

In order to solve the above-mentioned problem, the present disclosure provides a cellulose composition, comprising a plurality of biocelluloses having a diameter of from 20 to 30 nm and a length of from 2000 to 3000 nm. Owing to the hydroxyl group on the surface of the plurality of biocelluloses to form a hydrogen bonding force, the cellulose composition provides good stability.

In one embodiment, the biocellulose has an average diameter of 20 nanometers and an average length of 2000 nanometers.

When applying the cellulose composition of the present disclosure to a product which is applied on a surface layer of skin, the stability of the biocellulose can prolong the contacting time of the active ingredient with the skin, Also, owing to the high specific surface area of the cellulose composition, it is more compliant with the surfaces or pores of the skin to increase the contact area between the biocellulose and the skin, such that the transdermal absorption and substance transfer efficiency of the skin surface are improved, thereby providing skin moisturizing, anti-inflammatory, anti-aging, enhancing skin elasticity and absorbing secreted grease. In addition, the user does not have sticky and irritating feelings when applying, which is superior to a commercially available biocellulose layered material.

On the other hand, when the cellulose composition of the present disclosure is used as an agricultural fertilizer, the stability of the biocellulose can prevent from soil compaction, exert a good water storage and release effect, and promote the growth of plants or crops.

The cellulose composition has a higher specific surface area. The hydrophilicity, stability and biocompatibility of the cellulose composition are further improved by the high specific surface area of the cellulose composition, and the hydrogen bonding force provided by the hydroxyl group on the surface thereof.

In an embodiment of an aspect, the cellulose composition of the present disclosure is in the form of a frozen ingot, and the frozen ingot of the cellulose composition is obtained by freeze-drying treatment. Specifically, the product can be made into a frozen ingot by processes of low-temperature freezing, low-temperature and low-pressure pumping, as well as desorption, so that the stability of the whole product is improved that is not easy to deteriorate. Also, the biocellulose is excellent in rehydration, and is ready for use. In other words, the cellulose composition does not include a liquid medium. After adding 1 ml of water to the cellulose composition in the form of the frozen ingot to become a mixture, the biocellulose content in the mixture is greater than 0.4% by weight to 1.2% by weight, so as to provide a better dispersion rate. Specifically, after adding 1 ml of water to the cellulose composition in the form of a frozen ingot, the amount of the plurality of biocelluloses in the cellulose composition may be, for example, more than 0.4% by weight or 0.5% by weight, 0.6% by weight, 0.7% by weight, 0.8% by weight, 0.9% by weight, 1.0% by weight, 1.1% by weight, and 1.2% by weight.

The $OD_{620}$ value of the frozen ingot cellulose composition dispersed in 0.1 ml of water is greater than 0.29 to 1.22. The $OD_{620}$ value indicates the optical density measured at a light wavelength of 620 nm, and the $OD_{620}$ value of the frozen ingot cellulose composition dispersed in 0.1 ml of water may also be, for example, 0.295, 0.43, 0.53, 0.54, 0.65, 0.76, 0.88, 0.96, 0.98, 1.00, 1.13, 1.14, 1.21 and 1.22. In one embodiment, the $OD_{620}$ value is from 0.43 to 1.22. In another embodiment, the cellulose composition of the present disclosure is in a liquid state and further includes a liquid medium. For example, the liquid medium is water.

The liquid cellulose composition has good fluidity, and utilizes the high specific surface area of the cellulose composition to enhance the diffusion and dissolution effects of the active ingredient or drug. Further, when the cellulose composition containing water is dispersed in 0.1 ml of water, an $OD_{620}$ value of from 0.29 to 1.22 is obtained, for example, 0.295, 0.43, 0.53, 0.54, 0.65, 0.76, 0.88, 0.96, 0.98, 1.00, 1.13, 1.14, 1.21, and 1.22. In an embodiment of the present disclosure, the $OD_{620}$ value is from 0.43 to 1.22.

In the liquid cellulose composition of the present disclosure, the amount of the plurality of biocelluloses is more than 0.2 to 1.2% by weight, based on the total weight of the cellulose composition. If the amount of the plurality of biocelluloses is less than 0.2% by weight, due to insufficient hydroxyl groups of the plurality of biocelluloses to affect the interfacial tension of the liquid medium, the liquid medium and the plurality of biocelluloses are susceptible to aggregation by a cohesive force, resulting in delamination, which is not conducive to mixing. If the amount of the plurality of biocelluloses is higher than 1.2% by weight, there is no substantial benefit to the application effect, simply wasting resources. According to the present disclosure, in the cellulose composition of the present disclosure, the amount of the plurality of biocelluloses may be, for example, more than 0.2% by weight or 0.3% by weight, 0.4% by weight, 0.5% by weight, 0.6% by weight, 0.7% by weight, 0.8% by weight, 0.9% by weight, 1.0% by weight, 1.1% by weight, and 1.2% by weight, based on the total weight of the cellulose composition.

Further, in an embodiment of the present disclosure, the contact angle of the cellulose composition with a surface of sealing wax film (Parafilm) is from 95.5° to less than 107°.

The present disclosure further provides a cellulose composition comprising a plurality of biocelluloses having an aspect ratio (nm/nm) of from 66 to 150, and the $OD_{620}$ value of the cellulose composition dispersed in 0.1 ml of water is greater than 0.29 to 1.22.

According to the present disclosure, the cellulose composition may not include a liquid medium, and is in the form of a frozen ingot. The cellulose composition in the form of a frozen ingot becomes a mixture after being added with 1 ml of water, and the biocellulose content in the mixture is more than 0.4% by weight to 1.2% by weight to provide a better dispersion rate. Specifically, after adding 1 ml of water to the cellulose composition in the form of the frozen ingot to become a mixture, the amount of the plurality of biocelluloses in the mixture may be, for example, more than 0.4% by weight or 0.5% by weight, 0.6% by weight, 0.7% by weight, 0.8% by weight, 0.9% by weight, 1.0% by weight, 1.1% by weight, and 1.2% by weight. Certainly, the cellulose composition may also include a liquid medium such as water. Further, in the cellulose composition having a plurality of biocelluloses with an aspect ratio (nm/nm) of 66 to 150, an amount of the plurality of biocelluloses is greater than 0.2% by weight to 1.2% by weight based on the total weight of the cellulose composition. Further, a contact angle of the cellulose composition with a surface of sealing wax film (Parafilm) is from 95.5° to less than 107°.

The plurality of biocelluloses are formed by bacteria of at least one genus selected from the group consisting of *Gluconacetobacter*, *Acetobacter*, *Rhizobium*, *Sarcina*, *Pseudomonas*, *Achromobacter*, *Alcaligenes*, *Enterobacter*, *Azotobacter* and *Agrobacterium*.

In an embodiment of the present disclosure, the plurality of biocelluloses are formed by fermentation of strains of *Gluconacetobacter*, and specifically, *Gluconacetobacter xylinum*, which is characterized by an easy control of thickness of the obtained biocellulose.

The cellulose composition of the present disclosure may further comprise an organic nutrient, an active ingredient or a drug. Also, the presence of the plurality of biocelluloses does not affect the properties and activities of the organic nutrient, active ingredient or drug.

In an embodiment of the present disclosure, the organic nutrient includes waste crops after oil extraction or breakage and animal wastes. By adding organic nutrients to the cellulose composition, the cellulose composition can be used for agricultural purposes as a fertilizer to deliver nutrients in a stable and balanced manner.

In one embodiment of the present disclosure, the active ingredient is a moisturizing ingredient, a whitening ingredient, an anti-wrinkle ingredient, an exfoliating ingredient, an anti-inflammatory ingredient, a growth factor, or an enzyme.

The cellulose composition may further include other additives conventionally used in the art, for example, emulsifiers, penetration enhancers, softeners, solvents, excipients and antioxidants.

The cellulose composition of the present disclosure comprises a plurality of biocelluloses having a diameter of from 20 to 30 nm and a length of from 2000 to 3000 nm, and it greatly increases the specific surface area. As such, the cellulose composition increases a contact area between the biocelluloses and the skin surface when being applied to a product in contact with the skin, and the absorption and transmission efficiency of the substance are enhanced, thereby providing functions of skin moisturizing, anti-inflammatory, and anti-aging, and enhancing skin elasticity. When being applied to agricultural fertilizers, the cellulose composition can promote microbial growth and exert good water storage and release capacity.

DETAILED DESCRIPTION OF THE EMBODIMENTS

The embodiments of the present disclosure are described by way of specific examples, and those skilled in the art can readily conceive the advantages and functions of the present disclosure from the present disclosure. The present disclosure may be embodied or applied by other different embodiments, and the various details of the present disclosure may be variously modified and changed, based on different aspects and applications, without departing from the spirit and scope of the present disclosure. In addition, all of the ranges and values herein are inclusive and combinable. Any value or point falling within the ranges recited herein, such as any integer, may be the minimum or maximum value to derive the lower range and the like.

In order to obtain the cellulose composition of the present disclosure, a method for producing the above-described cellulose composition is as described below, comprising steps of: culturing, in a container with a culture solution, bacteria of at least one genus selected from the group consisting of *Gluconacetobacter*, *Acetobacter*, *Rhizobium*, *Sarcina*, *Pseudomonas*, *Achromobacter*, *Alcaligenes*, *Enterobacter*, *Azotobacter* and *Agrobacterium* for 24 to 96 hours. The culture solution has an agar, and a carbon source, peptone and a yeast extract at a weight ratio of from 5:1:1 to 4:1:1, so as to form a biocellulose membrane with a plurality of biocelluloses interwoven. In the presence of a liquid medium, the biocellulose membrane is homogeneously broken to obtain a dispersion. Based on the total weight of the cellulose composition, under a condition that the amount of the plurality of biocelluloses is greater than 0.2% by weight to 1.2% by weight, mechanical grinding is carried out on the plurality of biocelluloses, and the mechanically grounded dispersion is treated by ultrasonic vibration.

The term "static culturing" refers to a method in which bacteria form a layered biocellulose membrane on a surface of a culture solution in a nonwoven manner. In addition, the container used for the static culture is preferably a flat container for controlling the oxygen consumption of the bacteria through the lower container height, thereby achieving the regulation of the diameter of the biocellulose. On the other hand, since the network structure formed by the biocelluloses at a surface of the formed biocellulose membrane has a density larger than the one of the network structure inside the biocellulose membrane, the above static culturing and conditions are conducive to subsequently separate the plurality of the bioceluloses interwoven.

The term "biocellulose membrane" refers to a layer having a multi-layered network structure interwoven by a plurality of bioceluloses.

In an embodiment of an aspect, the formation of the biocellulose membrane is formed by statically culturing bacteria of *Gluconacetobacter* for fermentation in a culture solution having mannitol, peptone, yeast extract and agar, wherein the resulting biocellulose membrane has a water content of greater than 90%.

More specifically, the formation of the biocellulose membrane includes a culture solution in a container, wherein the composition of the culture solution comprises a carbon sources, a nitrogen source, and a gel support; the gel support is selected from an agar; the carbon source comprises saccharides or sugar alcohols such as mannitol and glucose; and the nitrogen source comprises peptone and yeast extract, and the carbon source, peptone and yeast extract may be at a weight ratio of from 5:1:1 to 4:1:1. Next, the pH of the culture solution is controlled at a pH of 0.5 to 6, and the microorganisms of the *Gluconobacter* are inoculated, and a range of the absorbance (optical density) of the microbial concentration in the culture solution (a set wavelength of 620 nm) is controlled to be between 0.006 to 0.01.

The culture environment is maintained at from 25 to 28° C., and the microorganisms are statically cultured for fermentation, and the biocellulose membrane is obtained after 24 to 96 hours, wherein the biocellulose membrane has a thickness of from 20 to 30 microns.

In an embodiment of an aspect, the biocellulose membrane has the biocellulose per unit area in an amount of from 0.0013 to 0.0018 g/cm$^2$ and the biocellulose has a diameter of from 20 to 100 nm.

The "homogeneous breakage" is carried out by mixing the biocellulose membrane with water, with a homogeneous equipment including a fixed outer cutter having a shearing force and a rotary inner knife having a saw blade shape to obtain a dispersion.

The solution configured for homogeneous breakage treatment may include any of the additives conventionally used in the art. For example, the method for producing the above composition of the present disclosure may include, after homogeneous breakage, a step of adding a treatment liquid to the dispersion to swell the biocellulose.

The "swelling or swelling treatment" is carried out by penetrating into the interior of the biocellulose through the treatment liquid, weakening the hydrogen bonding between the celluloses. The swelling treatment does not cause excessive hydrolysis of the biocellulose, and can also reduce the energy consumption of the mechanical grinding process. In combination with the synergistic effect of mechanical grinding shear, the glucan chain of the biocellulose is cleaved, the surface of the biocellulose is fibrillated, the specific surface area of the cellulose is increased, and more hydroxyl groups are exposed, so as to enhance the hydrophilicity and biocompatibility of the biocellulose.

The treatment liquid is at least one selected from the group consisting of an alkali solution, an inorganic salt solution, and an aqueous ionic liquid solution, wherein the alkali includes at least one selected from the group consisting of potassium hydroxide, sodium hydroxide and lithium hydroxide; the inorganic salt is at least one selected from the group consisting of zinc chloride, calcium chloride and magnesium chloride; the ionic liquid is at least one selected from the group consisting of 1-allyl-3-methylimidazolium chloride ([AMIm]Cl), 1-butyl-3-methylimidazolium chloride salt ([BMIm]Cl), 1-allyl-3-methylimidazolium acetate ([AMIm]Ac), 1-butyl-3-methylimidazolium acetate ([BMIm]Ac), lithium chloride/dimethylarylene (LiCl/DMSO), N-alkylpyridine and dialkyl imidazole. The treatment liquid can also be at least one selected from the group consisting of urea and urea sulfide.

The "mechanical grinding" is carried out by diluting the dispersion with water, and then grinding it with a horizontal ball mill device to fibrillate a surface of the biocellulose to have a diameter of from 20 to 30 nm and a diameter of from 2,000 to 3,000 nm. An amount of the plurality of bioceluloses for the mechanical grinding is greater than 0.2% by weight based on the total weight of the dispersion.

On the other hand, since the grounded biocellulose has a higher specific surface area, so the electrostatic effect, van der Waals force or hydrogen bonding force among the celluloses are more remarkable, and agglomeration occurs easily. Therefore, the method for producing the above composition of the present disclosure may include, after mechanical grinding, a step of ultrasonically oscillating the grounded dispersion to deagglomerate the agglomerates of the bioceluloses.

By applying the cellulose composition of the present disclosure to a product which is applied on a surface layer of the skin, the absorption and transmission efficiency of the substance are thus enhanced, and functions of the skin with moisturizing, anti-inflammatory, anti-aging and skin elasticity are provided as well.

In addition, the UV-resistant cellulose composition is tested for UV resistance. When the biocellulose content is 0.8% by weight or more, the UVA and UVB transmittances are less than 10%. When applying the cellulose composition of the present disclosure to a product applied on the surface of the skin, an anti-ultraviolet effect is further provided.

In addition, the cellulose composition of the present disclosure is used as an agricultural fertilizer, and the stability of the biocellulose can prevent soil compaction, and exert a good water storage and water release effect, achieving an effect of promoting microbial growth.

Test 1

Samples of the cellulose composition of various biocellulose contents were prepared according to the method described above, samples of specified contents of the cellulose composition and pure water were respectively dropped on a sealing wax film (Parafilm, PM-996) based on Table 1 below, and a contact angle of each of the samples of the cellulose composition was tested and recorded in Table 1 below.

TABLE 1

| No. | Biocellulose content (% by weight) | Contact angle test 1 | Contact angle test 2 | Contact angle test 3 | Contact angle average |
|---|---|---|---|---|---|
| Pure water | 0 | 108.065 | 108.197 | 106.241 | 107.501 |
| 1 | 0.2 | 104.591 | 107.270 | 106.375 | 106.079 |
| 2 | 0.4 | 89.964 | 98.733 | 99.111 | 95.936 |
| 3 | 0.6 | 100.553 | 97.371 | 99.575 | 99.166 |
| 4 | 0.8 | 103.099 | 98.833 | 96.563 | 99.498 |
| 5 | 1.0 | 102.346 | 108.385 | 97.136 | 102.622 |

According to the results shown in Table 1, when the cellulose composition of the present disclosure is dropped on the surface of the sealing wax film, as compared with the pure water dropped on the surface of the sealing wax film, the contact angle is less than 107°. Obviously, the cellulose composition of the present disclosure has excellent hydrophilicity.

Test 2

Samples of the cellulose composition of various biocellulose contents were prepared according to the method described above, and the biocelluloses of specified content were dispersed in 0.1 ml of water based on Table 2 below. An $OD_{620}$ value is measured; sedimentation is observed and checked with a naked eye for 3 days, and was recorded in Table 2 below.

TABLE 2

| No. | Biocellulose content (% by weight) | Sedimentation | $OD_{620}$ |
|---|---|---|---|
| 1 | 0.2 | Yes | 0.295 |
| 2 | 0.3 | No | 0.434 |
| 3 | 0.4 | No | 0.541 |
| 4 | 0.5 | No | 0.654 |
| 5 | 0.6 | No | 0.763 |
| 6 | 0.7 | No | 0.883 |
| 7 | 0.8 | No | 0.984 |
| 8 | 0.9 | No | 1.140 |
| 9 | 1.0 | No | 1.219 |

According to the results shown in Table 2, when the amount of the plurality of biocelluloses in the cellulose composition is 0.2% by weight or less, the liquid medium and the plurality of biocelluloses are easily affected by the cohesive force to agglomerate, causing delamination and sedimentation.

Test 3

Samples of the cellulose composition of various biocellulose contents were prepared according to the method described above, and the samples of the specified content of the cellulose composition were subjected to a viscosity test by a viscosity meter (Brookfield, rotor H02) according to Table 3 below. The results are recorded in Table 3.

TABLE 3

| No. | Biocellulose content (% by weight) | Test 1 (speed 50 rpm) | Test 1 (speed 100 rpm) | Average |
|---|---|---|---|---|
| 1 | 0.2 | 16 | 16 | 16 |
| 2 | 0.4 | 28.8 | 28 | 28.4 |
| 3 | 0.6 | 96 | 68 | 82 |
| 4 | 0.8 | 200 | 170.4 | 185.2 |
| 5 | 1.0 | 622.08 | 349.04 | 485.56 |

Test 4

Samples of the cellulose composition of various biocellulose contents were prepared according to the method described above, and samples of the specified content of the cellulose composition were made into frozen ingots based on Table 4 below, and the results whether the frozen ingots can be made were recorded.

TABLE 4

| No. | Biocellulose content (% by weight) | Made into frozen ingot | Volume of frozen ingot (ml) |
|---|---|---|---|
| 1 | 0.2 | No | X |
| 2 | 0.3 | No | X |
| 3 | 0.4 | No | X |
| 4 | 0.5 | Yes | 0.4 |
| 5 | 0.6 | Yes | 0.4 |
| 6 | 0.7 | Yes | 0.4 |
| 7 | 0.8 | Yes | 0.4 |
| 8 | 0.9 | Yes | 0.4 |
| 9 | 1.0 | Yes | 0.4 |

According to the results of Table 4, when the amount of the biocellulose in the aqueous cellulose composition is more than 0.4% by weight, the cellulose composition can be made into a frozen ingot product.

Test 5

Samples of the cellulose composition having an amount of 2% by weight of the plurality of biocelluloses were prepared according to the method described above, wherein the sample contained 0.1% by weight of L-ascorbic acid and the rest was saline.

In a container filled with pure water, a percutaneous absorption film (Strat-M, 3M Company) was placed therein, and a temperature of the pure water was maintained at 37° C. A lower surface of the percutaneous absorption film was in contact with pure water, and an upper surface was dropped with 5 ml of the sample. The absorbance ($OD_{280}$) in the water below the lower surface of the percutaneous absorption film was tested at different time points. Further, the method was repeated twice, and differences in absorbance at minute 0 and minute 60 were recorded, and an average value calculated from the difference of the absorbance values of the 2 times was 0.098.

On the other hand, the control sample containing no biocellulose was tested twice, and differences in absorbance at Minute 0 and Minute 60 were recorded, and an average value calculated by the difference of the absorbance values of the 2 times was 0.057. As such, the absorbance value of the sample using the cellulose composition of the present disclosure was more decreased, and it shall promote the transdermal absorption of L-ascorbic acid and enhance the antioxidant capacity.

Test 6

Samples of the cellulose composition having a content of 5% by weight of the plurality of biocelluloses were prepared according to the method described above, wherein the sample contained 10% by weight of arbutin and the rest was saline.

In a container filled with pure water, a percutaneous absorption film (Strat-M, 3M Company) was placed therein, and a temperature of the pure water was maintained at 37° C. A lower surface of the percutaneous absorption film was in contact with pure water, and an upper surface was dropped with 5 ml of the sample. The absorbance ($OD_{280}$) in the water below the lower surface of the percutaneous absorption film was tested at different time points, to convert a content of the arbutin. It was tested that at Minute 30 and Minute 60, the transdermally absorbed arbutin concentration of the sample of the cellulose composition of the present disclosure was increased from 25 μg/ml to 35 μg/ml, while in the control group containing no biocellulose, the arbutin measured at a concentration of about 25 μg/ml only at Minute 60. Obviously, the sample using the cellulose composition of the present disclosure promotes transdermal absorption of arbutin.

The above embodiments are merely illustrative, and are not intended to limit the present disclosure. Modifications and variations of the above-described embodiments can be made by those skilled in the art, without departing from the spirit and scope of the present disclosure. Therefore, the scope of the present disclosure is defined by the appended claims. As long as the effects and implementation purposes of the present disclosure are not affected, they should be encompassed in this technical content.

What is claimed is:

1. A cellulose composition in the form of a frozen ingot, comprising a plurality of biocelluloses formed by bacteria having a diameter of from 20 nm to 30 nm and a length of from 2000 nm to 3000 nm, wherein the cellulose composition does not comprise a liquid medium, and wherein after addition of 1 ml of water to the cellulose composition in the form of the frozen ingot to form a mixture, a content of the biocelluloses in the mixture is from 0.5% by weight to 1.2% by weight, and the plurality of the biocelluloses in the mixture do not agglomerate, wherein the plurality of the biocelluloses are formed by bacteria of at least one genus selected from the group consisting of *Gluconacetobacter, Acetobacter, Rhizobium, Sarcina, Pseudomonas, Achromobacter, Alcaligenes, Enterobacter, Azotobacter* and *Agrobacterium*.

2. The cellulose composition of claim 1, which has an OD620 value of from 0.29 to 1.22 when being dispersed in 0.1 ml of water.

3. The cellulose composition of claim 2, wherein the OD620 value is from 0.43 to 1.22.

4. The cellulose composition of claim 1, further comprising an organic nutrient, an active ingredient or a drug.

5. The cellulose composition of claim 4, wherein the active ingredient is a moisturizing component, a whitening component, an anti-wrinkle component, an exfoliating component, an anti-inflammatory component, a growth factor or an enzyme.

6. A cellulose composition in the form of a frozen ingot, comprising a plurality of biocelluloses formed by bacteria having an aspect ratio of from 66 to 150, wherein the cellulose composition does not comprise a liquid medium, wherein an OD620 value of the cellulose composition dispersed in 0.1 ml of water is from 0.29 to 1.22, and wherein after addition of 1 ml of water to the cellulose composition in the form of the frozen ingot to form a mixture, a content of the biocelluloses in the mixture is from 0.5% by weight to 1.2% by weight, and the plurality of the biocelluloses in the mixture do not agglomerate, wherein the plurality of the biocelluloses are formed by bacteria of at least one genus selected from the group consisting of *Gluconacetobacter, Acetobacter, Rhizobium, Sarcina, Pseudomonas, Achromobacter, Alcaligenes, Enterobacter, Azotobacter* and *Agrobacterium*.

7. The cellulose composition of claim 6, further comprising an organic nutrient, an active ingredient or a drug.

* * * * *